United States Patent
Cho et al.

(10) Patent No.: US 6,872,840 B1
(45) Date of Patent: Mar. 29, 2005

(54) SYNTHESIS OF 8-MEMBERED CARBOCYCLIC COMPOUND HAVING DIEXOMETHYLENE GROUPS

(75) Inventors: Yong Seo Cho, Seoul (KR); Moon Ho Chang, Seoul (KR); Hun Yeong Koh, Seoul (KR); Ae Nim Pae, Seoul (KR); Hyun Jung Kang, Seoul (KR)

(73) Assignee: Korea Institute of Science And Technology (KR)

( * ) Notice: Subject to any disclaimer, the term of this patent is extended or adjusted under 35 U.S.C. 154(b) by 0 days.

(21) Appl. No.: 10/823,708

(22) Filed: Apr. 14, 2004

(30) Foreign Application Priority Data

Sep. 17, 2003 (KR) .................................. 10-2003-0064384

(51) Int. Cl.$^7$ ..................... C07D 311/02; C07D 311/78; C07D 311/94
(52) U.S. Cl. ..................... 549/397; 549/383; 549/386
(58) Field of Search ............................... 549/397, 383, 549/386

(56) References Cited

PUBLICATIONS

Article "The 91$^{st}$ National Meeting of the Korean Chemical Society", ISSN 1229–6708, Apr. 18–19, 2003, p. 363.
Paul A. Wender, et al., "Transition Metal–Catalyzed [6+2] Cycloadditions of 2–Vinylcyclobutanones and Alkenes: A New Reaction for the Synthesis of Eight–Membered Rings", J. Am. Chem. Soc., vol. 122, No. 32, 2000 American Chemical Society, pp. 7815–7816.
Scott R. Gilbertson, et al., "Rhodium Catalyzed [4+2+2] Cycloaddition and Alkyne Insertion: A New Route to Eight–Membered Rings", J. Am. Chem. Soc., vol. 124, No. 30, 2002, American Chemical Society, pp. 8784–8785.

Primary Examiner—Ba K. Trinh
(74) Attorney, Agent, or Firm—Lowe Hauptman & Berner

(57) ABSTRACT

The present invention relates to a synthesis of an 8-membered carbocyclic compound having diexomethylene groups, more particularly to a synthesis of an 8-membered carbocyclic compound having diexomethylene groups, a novel compound having the structure represented by the following Chemical Formula 1, from trimethylsilanyl-methyl-allenol derivative by the intramolecular Prins cyclization using Lewis acid. The 8-membered carbocyclic compound is a useful intermediate for synthesis of other multicarbocyclic compounds.

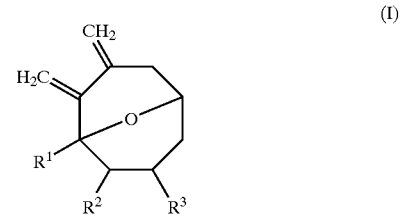

(I)

In Chemical Formula 1, $R^1$ is a phenyl group, and $R^2$ and $R^3$ is a hydrogen atom, or $R^1$, $R^2$ and $R^3$ may be connected with neighboring substituents to form a 5 to 10-membered aliphatic or aromatic ring.

19 Claims, No Drawings

SYNTHESIS OF 8-MEMBERED CARBOCYCLIC COMPOUND HAVING DIEXOMETHYLENE GROUPS

BACKGROUND OF THE INVENTION

1. Field of the Invention

The present invention relates to a synthesis of an 8-membered carbocyclic compound having diexomethylene groups, more particularly to a synthesis of an 8-membered carbocyclic compound having diexomethylene groups, a novel compound having the structure represented by the following Chemical Formula 1, from trimethylsilanyl-methyl-allenol derivative by the intramolecular Prins cyclization using Lewis acid. The 8-membered carbocyclic compound is a useful intermediate for synthesis of other multicarbocyclic compounds.

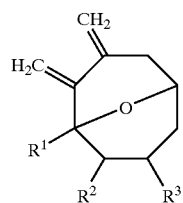

(I)

In Chemical Formula 1, $R^1$ is a phenyl group, and $R^2$ and $R^3$ is respectively a hydrogen atom, or $R^1$, $R^2$ and $R^3$ may be connected with neighboring substituents to form a 5 to 10-membered aliphatic or aromatic ring.

2. Description of the Related Art 8-membered carbocyclic compounds are important ingredients of biologically active natural substances and medicines. Recently, they are gaining interest in genetics because they are known to take part in cell division. For example, Taxol, which is widely known as anticancer drug [Taxane Anticancer Agents, ACS Symposium Series 583], has an 8-membered ring. Besides, since 8-membered carbocyclic compounds have good biological activities, development of an 8-membered carbocyclic compound with a new structure is a prerequisite for drug researches.

A carbocyclic compound having diexomethylene groups can be expanded to other multicarbocyclic compounds through Diels-Alder reactions. Therefore, the compound represented by Chemical Formula 1, which has diexomethylene groups, is a very useful intermediate in synthesizing a multicarbocyclic compound via Diels-Alder reactions.

SUMMARY OF THE INVENTION

It is an object of the present invention to provide an 8-membered carbocyclic compound having diexomethylene groups, which is represented by Chemical Formula.

It is another object of the present invention to provide a method for synthesizing the novel compound represented by Chemical Formula 1 from a trimethylsilanylmethyl-allenol derivative by the intramolecular Prins cyclization using Lewis acid.

DETAILED DESCRIPTION OF THE PREFERRED EMBODIMENTS

The present invention is characterized by an 8-membered carbocyclic compound having a new structure, which is represented by the following Chemical Formula 1:

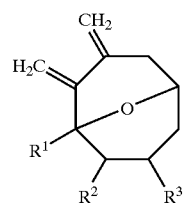

(I)

In Chemical Formula 1, $R^1$ is a phenyl group, and $R^2$ and $R^3$ is respectively a hydrogen atom, or $R^1$, $R^2$ and $R^3$ may be connected with neighboring substituents to form a 5 to 10-membered aliphatic or aromatic ring.

Also, the present invention is characterized by a method of synthesizing the compound represented by Chemical Formula 1 from a trimethylsilanylmethyl-allenol derivative by the intramolecular Prins cyclization in the presence of Lewis acid.

Hereinafter, the present invention is described in more detail.

The 8-membered carbocyclic compound represented by Chemical Formula 1, which is provided by the present invention, is a novel compound having diexomethylene groups, and it can be used as an active ingredient of medicines, or intermediate of synthesizing multicarbocyclic compounds in the field of medicine and precise chemistry.

Specific examples of the compound provided by the present invention include:

a compound wherein $R^1$ is a phenyl group, and $R^2$ and $R^3$ is respectively a hydrogen atom;

a compound wherein $R^1$ and $R^2$ are connected with each other to form a 5 to 10-membered aliphatic or aromatic ring, and $R^3$ is a hydrogen atom; and a compound wherein $R^2$ and $R^3$ are connected with each other to form a 5 to 10-membered aliphatic or aromatic ring, and $R^1$ is a hydrogen atom.

The present invention also provides a method of synthesizing the compound represented by Chemical Formula 1 from a trimethylsilanylmethyl-allenol derivative by the intramolecular Prins cyclization in the presence of Lewis acid.

For the Lewis acid, such common Lewis acids as trimethylsilyl trifluoromethanesulfonate (TMSOTf) or indium halide ($InX_3$, X=Cl or Br) can be used. Most preferably, TMSOTf is used. Preferably, the Lewis acid is used in 1.0 to 1.5 equivalent of the starting material, trimethylsilanylmethyl-allenol derivative. For the reaction solvent, common organic solvents such as diethyl ether, tetrahydrofuran, dichloromethane, chloroform and ethyl acetate can be used. Most preferably, diethyl ether is used. The reaction was performed at from −90° C. to room temperature (25° C.) for about 3 to 5 hours.

Since the aforementioned intramolecular Prins cyclization is industrially very probable because it is relatively simple and offers good yield.

The compound represented by Chemical Formula 1 is useful in the field of medicine and precise chemistry. Because the compound represented by Chemical Formula 1 has diexomethylene groups, other multicarbocyclic compounds can be prepared from it via Diels-Alder reactions.

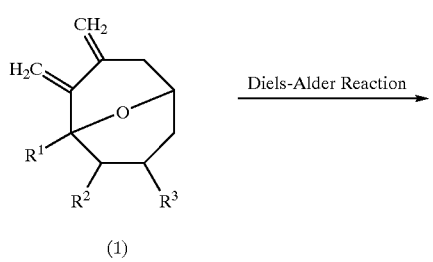

(1)

Hereinafter, the present invention is described in more detail through Examples. However, the following Examples should not be construed as limiting the scope of the present invention.

EXAMPLES

Example 1

Synthesis of 2,3-dimethylene-1-phenyl-9-oxa-bicyclo[3.3.1]nonane

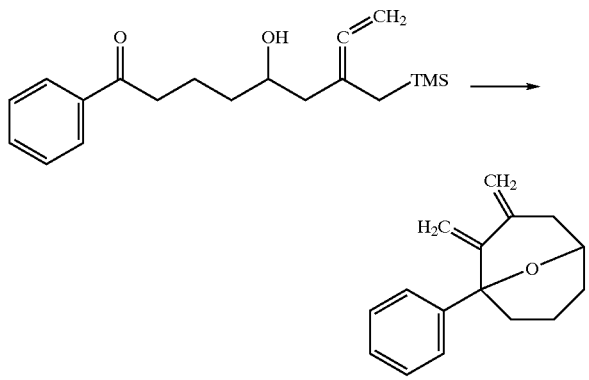

1.50 mL of diethyl ether was added to 5-hydroxy-1-phenyl-7-trimethylsilanylmethyl-nona-7,8-diene-2-one (117 mg, 0.37 mmol) under nitrogen atmosphere. While stirring at −78° C., trimethylsilyl trifluoromethanesulfonate (TMSOTf; 67 μL, 0.37 mmol) was added. While stirring the reaction mixture, the reaction temperature was slowly increased to room temperature for 3 hours. The reaction mixture was stirred at room temperature for 30 minutes. After the reaction was completed, H$_2$O was added. After stirring for about 5 minutes, the reaction mixture was diluted with ethyl acetate (EtOAc) and washed with water and saturated brine. The organic layer was separated from the reaction mixture and dried with anhydrous magnesium sulfate (MgSO$_4$). The solvent was removed under reduced pressure and the remaining material was purified with column chromatography (EtOAc/n-hexane=1/7) to obtain 82 mg of the product (98%). $^1$H NMR(300 MHz, CDCl$_3$) δ 7.43 (d, 2H, J=1.5 Hz), 7.21 (m, 3H), 5.17 (s, 1H), 5.07 (s, 1H), 4.72 (s, 1H), 4.33 (s, 1H), 4.13 (s, 1H), 3.00 (m, 1H), 2.40 (d, 1H, J=14.8 Hz), 2.19 (m, 2H), 1.94 (m, 2H), 1.60 (m, 2H); $^{13}$C NMR (75 MHz, CDCl$_3$) δ 152.5, 147.0, 146.0, 128.2, 127.4, 126.4, 111.7, 109.4, 77.7, 69.5, 38.7, 36.7, 30.6, 17.8 ppm.

Example 2

Synthesis of 11,12-dimethylene-13-oxa-tricyclo[7.3.1.0$^{2,7}$]trideca-2,4,6-triene

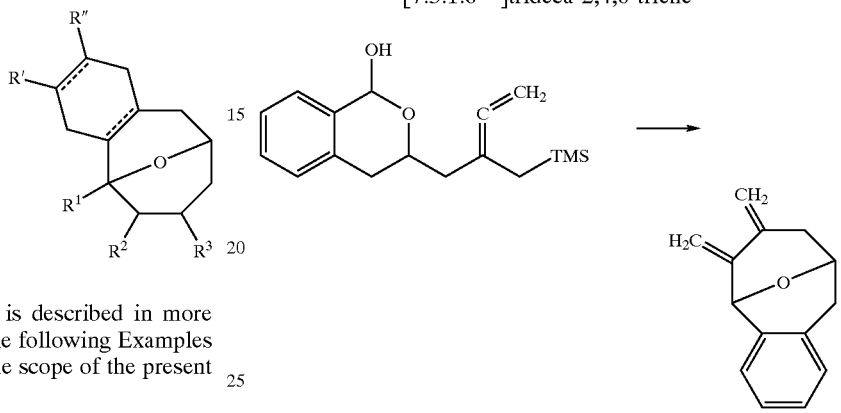

1.20 mL of diethyl ether was added to 3-(2-trimethylsilanylmethyl-buta-2,3-dienyl)-isochroman-1-ol (78 mg, 0.27 mmol) under nitrogen atmosphere. While stirring at −78° C., TMSOTf (49 μL, 0.27 mmol) was added. While stirring the reaction mixture, the reaction temperature was slowly increased to room temperature for 3 hours. The reaction mixture was stirred at room temperature for 30 minutes. After the reaction was completed, H$_2$O was added. After stirring for about 5 minutes, the reaction mixture was diluted with EtOAc and washed with water and saturated brine. The organic layer was separated from the reaction mixture and dried with anhydrous MgSO$_4$. The solvent was removed under reduced pressure and the remaining material was purified with column chromatography (EtOAc/n-hexane=1/6) to obtain 42 mg of the product (78%).

$^1$H NMR (300 MHz, CDCl$_3$) δ 7.15 (m, 3H), 7.03 (d, 1H, J=8.7 Hz), 5.26 (s, 1H), 5.04 (d, 1H, J=9.3 Hz), 4.94 (s, 1H), 4.76 (s, 1H), 4.65 (t, 1H, J=6.9 Hz), 3.41 (dd, 1H, J$_1$=17.4 Hz, J$_2$=7.8 Hz), 2.98 (bd, 1H, J=12 Hz), 2.66 (d, 1H, J=17.1 Hz), 2.65 (d, 1H, J=14.7 Hz); $^{13}$C NMR (75 MHz, CDCl$_3$) δ 148.55, 140.89, 137.33, 132.00, 128.75, 127.21, 125.98, 125.56, 112.28, 107.38, 77.73, 68.34, 40.79, 32.12 ppm.

Example 3

Synthesis of 10,11-dimethylene-12-oxa-tricyclo[6.3.1.0$^{1,5}$]dodecane

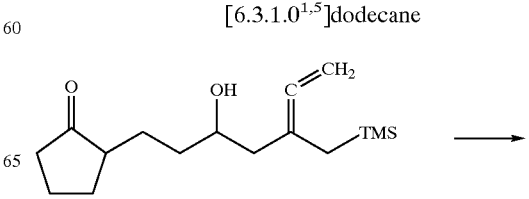

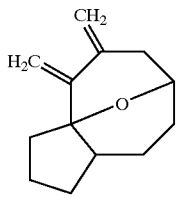

1.50 mL of diethyl ether was added to 2-(3-hydroxy-5-trimethylsilanylmethyl-hepta-5,6-dienyl)-cyclopentanone (98 mg, 0.35 mmol) under nitrogen atmosphere. While stirring at −78° C., TMSOTf (63 μL, 0.35 mmol) was added. While stirring the reaction mixture, the reaction temperature was slowly increased to room temperature for 3 hours. The reaction mixture was stirred at room temperature for 30 minutes. After the reaction was completed, $H_2O$ was added. After stirring for about 5 minutes, the reaction mixture was diluted with EtOAc and washed with water and saturated brine. The organic layer was separated from the reaction mixture and dried with anhydrous $MgSO_4$. The solvent was removed under reduced pressure and the remaining material was purified with column chromatography (EtOAc/n-hexane=1/15) to obtain 60 mg of the pro duct (91%).

$^1$H NMR (300 MHz, $CDCl_3$) δ 5.17 (s, 1H), 5.11 (s, 1H), 4.86 (s, 1H), 4.79 (s, 1H), 4.22 (s, 1H), 2.35 (d, 1H, J=18 Hz) 2.16 (m, 3H), 1.79 (m, 6H), 1.42 (m, 2H); $^{13}$C NMR (75 MHz, $CDCl_3$) δ 150.68, 146.09, 128.21, 109.58, 106.38, 68.83, 45.06, 39.23, 37.71, 29.32, 25.07, 21.62, 20.28 ppm.

Comparative Example

Diels-Alder Reaction using 11,12-dimethylene-13-oxa-tricyclo [7.3.1.0$^{2,7}$]trideca-2,4,6-triene The following is an example of synthesizing another multicarbocyclic compound by Diels-Alder from the compound represented by Chemical Formula 1.

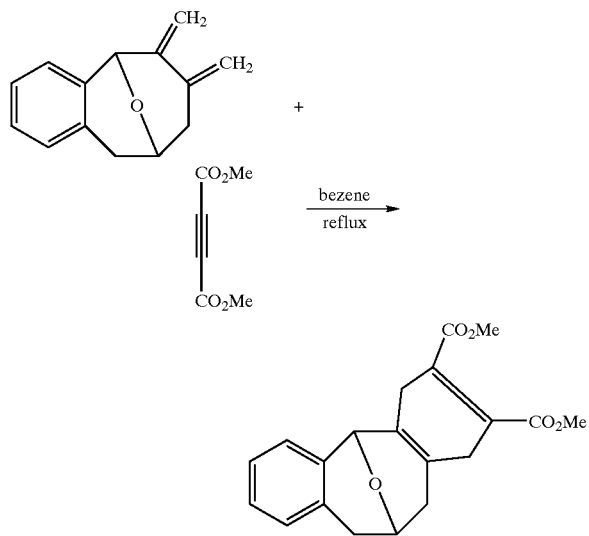

2.0 mL of benzene was added to 11,12-dimethylene-13-oxa-tricyclo[7.3.1.0$^{2,7}$]trideca-2,4,6-triene (42 mg, 0.2 mmol) under nitrogen atmosphere. After adding dimethylacetylene dicarboxylate (85.62 mg, 0.6 mmol), the reaction mixture was stirred with reflux at 85° C. for 5 hours. After the reaction was completed, $H_2O$ was added. After stirring for about 5 minutes, the reaction mixture was diluted with ethyl acetate and washed with water and saturated brine. The organic layer was separated from the reaction mixture and dried with anhydrous $MgSO_4$. The solvent was removed under reduced pressure and the remaining material was purified with column chromatography (EtOAc/n-hexane=1/6) to obtain 42 mg of the product (62%).

$^1$H NMR (300 MHz, $CDCl_3$) δ 7.18 (m, 4H), 5.44 (d, 1H, J=5.97 Hz), 4.90 (s, 1H), 3.82 (s, 1H), 3.71 (s, 1H), 2.87 (m, 7H).

As described above, the present invention offers the following advantages:

1) Dimethylene carbocyclic compounds having a variety of structures can be synthesized using trimethylsilanylmethyl-allenol derivative as a starting material.
2) The synthesis reaction is simple.
3) The synthesis yield is high.
4) The diexomethylene carbocyclic compound is useful as an intermediate of synthesizing multicarbocyclic compounds having an 8-membered ring, which are very important in the field of precise chemistry, by Diels-Alder reactions.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. An 8-membered carbocyclic compound with diexomethylene groups having the formula (I):

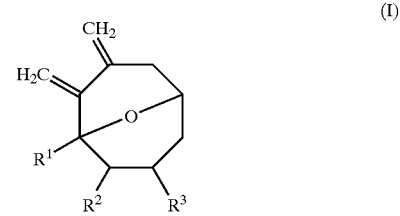

(I)

wherein $R^1$ is a phenyl group, and $R^2$ and $R^3$ is each a hydrogen atom, or $R^1$, $R^2$ and $R^3$ are connected with neighboring substituents to form a 5 to 10-membered aliphatic or aromatic ring.

2. The compound of claim 1, wherein $R^1$ is a phenyl group, and $R^2$ and $R^3$ is each a hydrogen atom.

3. The compound of claim 1, wherein $R^1$ and $R^2$ are connected with each other to form a 5 to 10-membered aliphatic or aromatic ring, and $R^3$ is a hydrogen atom.

4. The compound of claim 1, wherein $R^2$ and $R^3$ are connected with each other to form a 5 to 10-membered aliphatic or aromatic ring, and $R^1$ is a hydrogen atom.

5. The compound of claim 4, wherein $R^2$ and $R^3$ are connected with each other to form a phenyl ring.

6. The compound of claim 3, wherein $R^1$ and $R^2$ are connected with ech other to form a cyclopentyl ring.

7. A method of synthesizing an 8-membered carbocyclic compound with diexomethylene groups having the formula (I), which comprises reacting a trimethylsilanylmethyl-allenol compound by an intramolecular Prins cyclization in the presence of a Lewis acid:

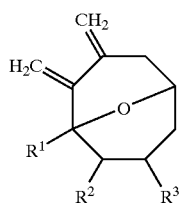 (I)

wherein R¹ is a phenyl group, and R² and R³ is each hydrogen atom, or R¹, R² and R³ are connected with neighboring substituents to form a 5 to 10-membered aliphatic or aromatic ring.

8. The method of claim 7, wherein said reaction is conducted in the presence of a solvent selected from the group consisting of diethyl ether, tetrahydrofuran, dichloromethane and chloroform.

9. The method of claim 7, wherein said Lewis acid is trimethylsilyl trifluoromethanesulfonate (TMSOTf) and is used in an amount of 1.0 to 1.5 equivalent of said trimethylsilanylmethyl-allenol compound.

10. The method of claim 7, which said reaction is conducted at a temperature in the range of from −90° C. to 25° C.

11. The method of claim 10, wherein said reaction is conducted at −78° C.

12. The method of claim 8, wherein said solvent is diethyl ether.

13. The method of claim 7, wherein said reaction is conducted for about 3 to 5 hours.

14. The method of claim 7, wherein the 8-membered carbocyclic compound is 2,3-dimethylene-1 phenyl-9-oxa-bicyclo[3.3.1]nonane.

15. The method of claim 7, wherein the 8-membered carbocyclic compound is 11,12-dimethylene-13-oxa-tricyclo[7.3.1.0$^{2,7}$]trideca-2,4,6-triene.

16. The method of claim 7, wherein the 8-membered carbocyclic compound is 10,11-dimethylene-12-oxa-tricyclo[6.3.1.0$^{1,5}$]dodecane.

17. The method of preparing an 8-membered carbocyclic compound, which comprises effecting an intramolecular Prins cyclization of a trimethylsilanylmethyl-allenol compound in the presence of a Lewis acid with a yield of at least 78%.

18. The method of claim 17, wherein said yield is at least 91%.

19. A method of preparing a Diels-Alder reaction product, which comprises subjecting the 8-membered carbocyclic compound of claim 1, to a Diels-Adler reaction.

\* \* \* \* \*